(12) United States Patent
Perouse

(10) Patent No.: US 9,895,152 B2
(45) Date of Patent: Feb. 20, 2018

(54) KIT FOR MANEUVERING AN ELEMENT PRESENT IN THE BODY OF A PATIENT, COMPRISING AN IMPLANTABLE CHAMBER

(75) Inventor: Eric Perouse, Paris (FR)

(73) Assignee: PEROUSE MEDICAL, Ivry le Temple (FR)

( * ) Notice: Subject to any disclaimer, the term of this patent is extended or adjusted under 35 U.S.C. 154(b) by 287 days.

(21) Appl. No.: 14/342,330

(22) PCT Filed: Aug. 30, 2012

(86) PCT No.: PCT/EP2012/066911
§ 371 (c)(1),
(2), (4) Date: Mar. 12, 2014

(87) PCT Pub. No.: WO2013/030305
PCT Pub. Date: Mar. 7, 2013

(65) Prior Publication Data
US 2014/0213988 A1    Jul. 31, 2014

(30) Foreign Application Priority Data

Sep. 2, 2011    (FR) ...................................... 11 57814

(51) Int. Cl.
*A61B 17/12*    (2006.01)
*A61M 5/142*    (2006.01)
(Continued)

(52) U.S. Cl.
CPC ........... *A61B 17/12* (2013.01); *A61M 5/1428* (2013.01); *A61M 39/0208* (2013.01); *A61M 39/04* (2013.01)

(58) Field of Classification Search
CPC ................ A61M 5/1428; A61M 39/02; A61M 39/0208; A61M 39/04; A61B 17/12;
(Continued)

(56) References Cited

U.S. PATENT DOCUMENTS 3,730,186 A * 5/1973 Edmunds, Jr. ....... A61B 17/122
                                                                    128/DIG. 25
3,749,098 A * 7/1973 De Bennetot ......... A61F 2/0036
                                                                           251/65
(Continued)

FOREIGN PATENT DOCUMENTS

WO    WO 2007/051563 A1    5/2007
WO    WO 2007/138590 A2    12/2007

OTHER PUBLICATIONS http://www.thefreedictionary.com/septum, retrieved Aug. 10, 2016.*
(Continued)

*Primary Examiner* — David C Eastwood
(74) *Attorney, Agent, or Firm* — Knobbe, Martens, Olson & Bear, LLP

(57) ABSTRACT

A kit according to the invention includes a tool and an implantable chamber. The implantable chamber comprises a hollow main body delimiting an internal volume opening outwards via a main opening. It further comprises a septum mounted on the main body to close the main opening, and at least one conduit extending from the main body. It also comprises a displacement member, movable relative to the main body, that projects from the main body via the conduit and actuates or sets in motion an element situated in the body of the patient. It lastly comprises a drive mechanism for driving the displacement member situated in the internal volume of the main body, in order to move the displacement member with respect to the main body. The tool includes a proximal maneuvering region and a distal region that is capable of piercing the septum to actuating the drive mechanism.

16 Claims, 7 Drawing Sheets

(51) Int. Cl.
*A61M 39/02* (2006.01)
*A61M 39/04* (2006.01)

(58) Field of Classification Search
CPC ........ A61B 17/12009; A61B 17/12013; A61B 2017/12004; A61B 2017/12018; A61F 5/0009; A61F 5/0013; A61F 5/003; A61F 5/005–5/0089
See application file for complete search history.

(56) References Cited

U.S. PATENT DOCUMENTS

| | | | | |
|---|---|---|---|---|
| 3,840,018 A * | 10/1974 | Heifetz | ............ | A61B 17/12009 24/16 PB |
| 4,548,201 A * | 10/1985 | Yoon | ........................ | A61F 6/202 128/831 |
| 4,557,722 A * | 12/1985 | Harris | ............... | A61M 5/14276 604/891.1 |
| 5,158,547 A | 10/1992 | Doan et al. | | |
| 6,074,341 A * | 6/2000 | Anderson | ............. | A61F 2/0036 128/DIG. 25 |
| 6,709,385 B2 * | 3/2004 | Forsell | ................. | A61F 2/0036 128/DIG. 25 |
| 7,207,936 B2 * | 4/2007 | Forsell | ..................... | A61F 2/26 600/38 |
| 7,282,023 B2 * | 10/2007 | Frering | .................. | A61F 2/004 600/31 |
| 7,288,064 B2 * | 10/2007 | Boustani | ............... | A61F 5/0066 600/31 |
| 8,517,915 B2 * | 8/2013 | Perron | ................. | A61F 5/0056 600/37 |
| 8,617,049 B2 * | 12/2013 | Dlugos, Jr. | ........... | A61F 2/0036 600/29 |
| 8,961,393 B2 * | 2/2015 | Rion | ..................... | A61F 5/0053 600/37 |
| 9,028,394 B2 * | 5/2015 | Honaryar | ................ | A61F 5/005 600/37 |
| 2001/0011543 A1 * | 8/2001 | Forsell | ................. | A61B 17/135 128/899 |
| 2002/0111530 A1 * | 8/2002 | Bakane | ................. | A61F 2/0036 600/30 |
| 2002/0198548 A1 * | 12/2002 | Robert | ................. | A61B 17/135 606/157 |
| 2003/0032857 A1 * | 2/2003 | Forsell | ................. | A61F 2/0036 600/30 |
| 2005/0055025 A1 * | 3/2005 | Zacouto | ................. | A61B 17/68 623/17.12 |
| 2006/0161186 A1 * | 7/2006 | Hassler, Jr. | ........... | A61F 5/0053 606/153 |
| 2007/0167672 A1 * | 7/2007 | Dlugos | ................. | A61F 5/0066 600/37 |
| 2007/0213751 A1 * | 9/2007 | Scirica | ................. | A61F 5/0066 606/157 |
| 2011/0071553 A1 * | 3/2011 | Dlugos, Jr. | ........... | A61F 2/0036 606/151 |
| 2014/0249573 A1 * | 9/2014 | Arav | ................ | A61B 17/12013 606/202 |

OTHER PUBLICATIONS http://www.thefreedictionary.com/pierce, retrieved Aug. 14, 2012.*
International Search Report re International Application No. PCT/EP2012/066911, dated Jan. 7, 2013, in 6 pages.

* cited by examiner

KIT FOR MANEUVERING AN ELEMENT PRESENT IN THE BODY OF A PATIENT, COMPRISING AN IMPLANTABLE CHAMBER

CROSS-REFERENCE TO RELATED APPLICATIONS

This application is a U.S. National Phase of International Application No.: PCT/EP2012/066911, filed Aug. 30, 2012, designating the U.S., and published in French as WO 2013/030305 on Mar. 7, 2013, which claims the benefit of French Patent Application No. 1157814 filed Sep. 2, 2011.

The present invention relates to an implantable chamber designed to be placed under the skin of a patient, comprising:

a hollow main body delimiting an internal volume, the internal volume opening outwards via a main opening, a septum mounted on the main body to close the main opening, at least one conduit projecting away from the main body.

Such an implantable chamber is used to provide a favored access point into the body of a patient, when frequent manipulations must be done, to inject a fluid into the patient. However, the implantable chambers are used only for that injection and therefore have limited functionalities.

Furthermore, medical devices exist for ligating an organ or vessel, for example in the cardiovascular surgery field, or for remotely actuating a device implanted in the body of a patient, for example a pump.

Such devices, however, require direct access to the organ to be ligated or the object to be actuated, by opening the skin of the patient. Thus, if a practitioner must regularly tighten, loosen or actuate the same external object, he may be required to open and suture the patient's body several times in the location where such operations are done. This may be very restrictive, both for the patient and the practitioner.

One aim of the invention is to obtain an implantable chamber having improved functionalities.

To that end, the invention relates to an implantable chamber of the aforementioned type, characterized in that it includes:

a displacement member that is movable relative to the main body capable of projecting from the main body via the or each conduit and capable of actuating or setting in motion an element situated in the body of a patient, and a drive mechanism for driving the displacement member situated in the internal volume of the main body, in order to move the displacement member with respect to the main body.

According to other embodiments, the implantable chamber comprises one or more of the following features, considered alone or according to all technically possible combinations:

the implantable chamber includes a centering member mounted below the septum within the internal volume of the main body, the centering member being capable of guiding the movement of a tool longitudinally along a centering axis, the septum is designed to be pierced by said tool and the drive mechanism is capable of cooperating with said tool, the centering member includes an inner surface converging toward a centering opening situated in register with the drive mechanism, the drive mechanism includes a member rotatably mounted in the internal volume, the displacement member being engaged on the rotating member, the axis of rotation of the rotating member is combined with the centering axis of the centering member, the rotating member comprises a head delimiting a housing for receiving a tool for actuating the drive mechanism, the rotating member has a toothed pinion, the displacement member defining orifices spaced along its length to cooperate with the toothed pinion on the rotating member, the displacement member comprises notches capable of cooperating with the rotating member, the implantable chamber includes means for locking the drive mechanism situated within the internal volume of the main body, the locking means being able to be released when the actuating tool for actuating the drive mechanism is inserted, the drive mechanism includes a drive member for driving the displacement member, movable between a locked position and a released position, the locking means including:

a member for engaging the displacement member in the locked position, and an elastic bias member for biasing the moving member toward its locked position;

the displacement member is capable of actuating or setting in motion an element situated in the body of the patient, such as an external object or member, without injecting fluid outside the main body;

the movable displacement member is made up of a chain, advantageously toothed, a rack or a thread.

The invention further relates to a kit for remotely maneuvering an element present in the body of a patient, of the type comprising a tool including a proximal maneuvering region and a distal region capable of piercing a septum, characterized in that the implantable chamber is as defined above and in that the tool is capable of actuating the drive mechanism of the implantable chamber.

The invention also relates to a method for remotely maneuvering an element present in the body of a patient, the method comprising the following steps:

providing a kit as defined above, piercing the tool through the septum to insert the distal region of the tool into the internal volume, engaging the tool on the drive mechanism, actuating the drive mechanism using the tool to move the displacement member.

The invention will be better understood upon reading the following description, provided solely as an example and done in reference to the appended drawings, in which.

Figure 1:
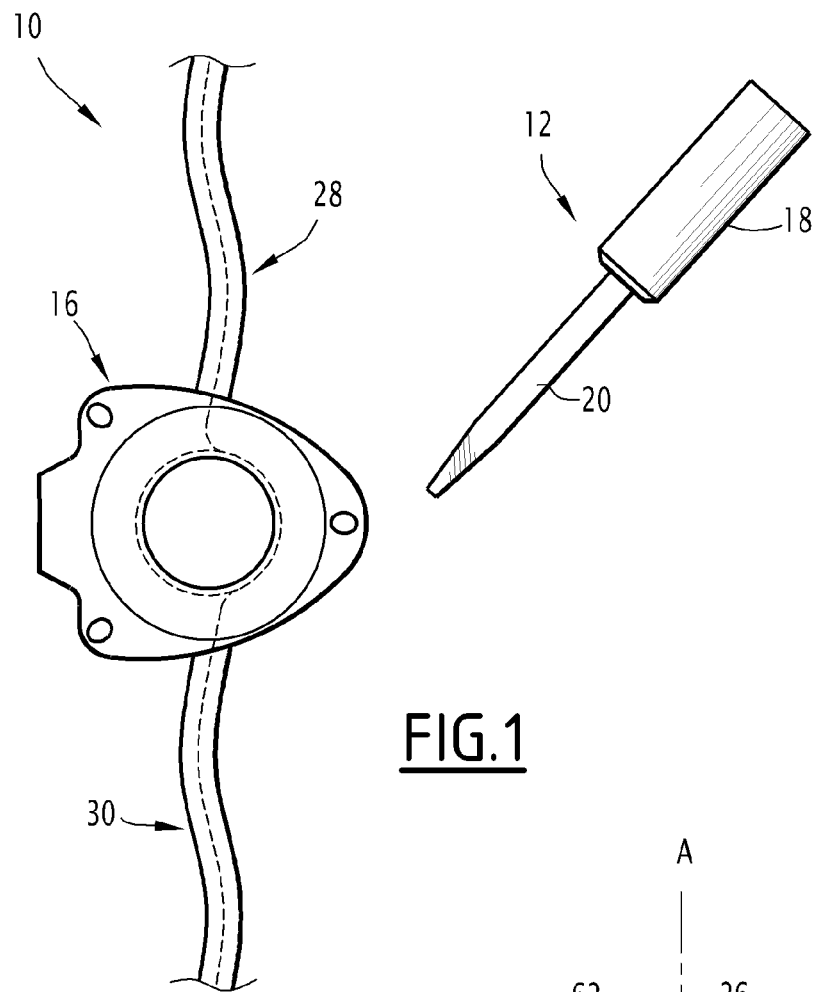
FIG. 1 is a diagrammatic view of a first kit according to the invention for remotely actuating an external object in the body of a patient, including an actuating tool and an implantable chamber.

A first kit 10 for remotely actuating an external object in the body of a patient 11 is shown in FIG. 1. Such a kit 10 is in particular capable of remotely actuating an element situated in the body of the patient 11, such as an external object or an organ.

The kit 10 includes a tool 12 designed to be inserted through the skin 14 of the patient 11 and to actuate a drive mechanism, and a first implantable chamber 16 according to the invention, positioned under the skin 14 of the patient.

The external object is for example a medical pump 17 situated in the body of the patient.

The tool 12 includes a proximal maneuvering region 18 capable of being grasped by a user and a distal region 20 capable of piercing a septum of the chamber 16 and actuating a drive mechanism.

Figure 2:
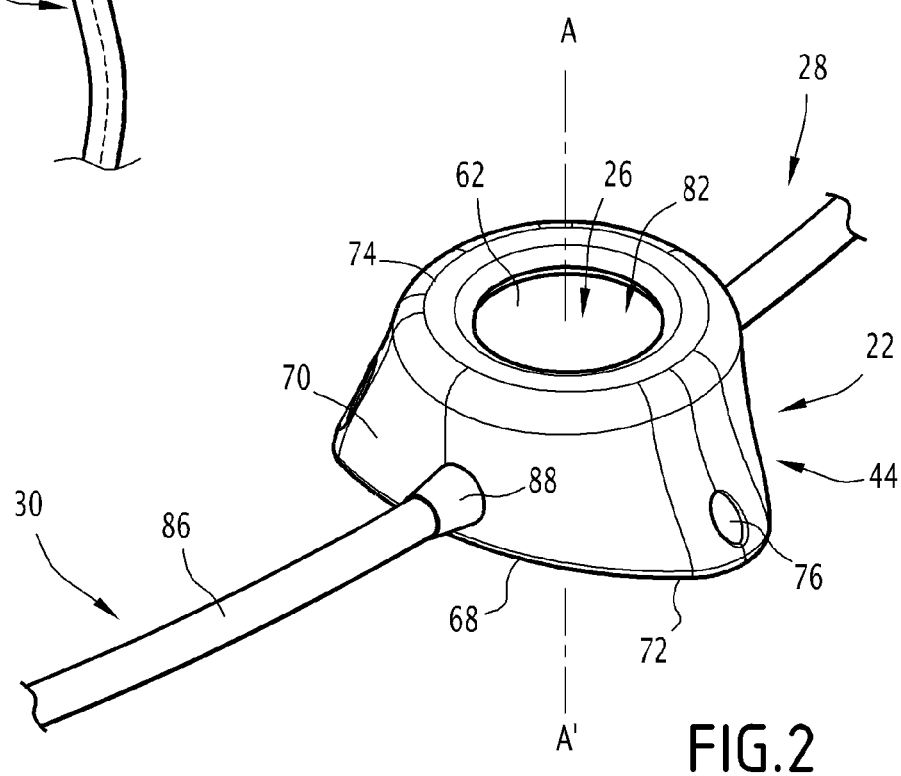
FIG. 2 is an outer perspective view of the implantable chamber of FIG. 1.
Figure 3:
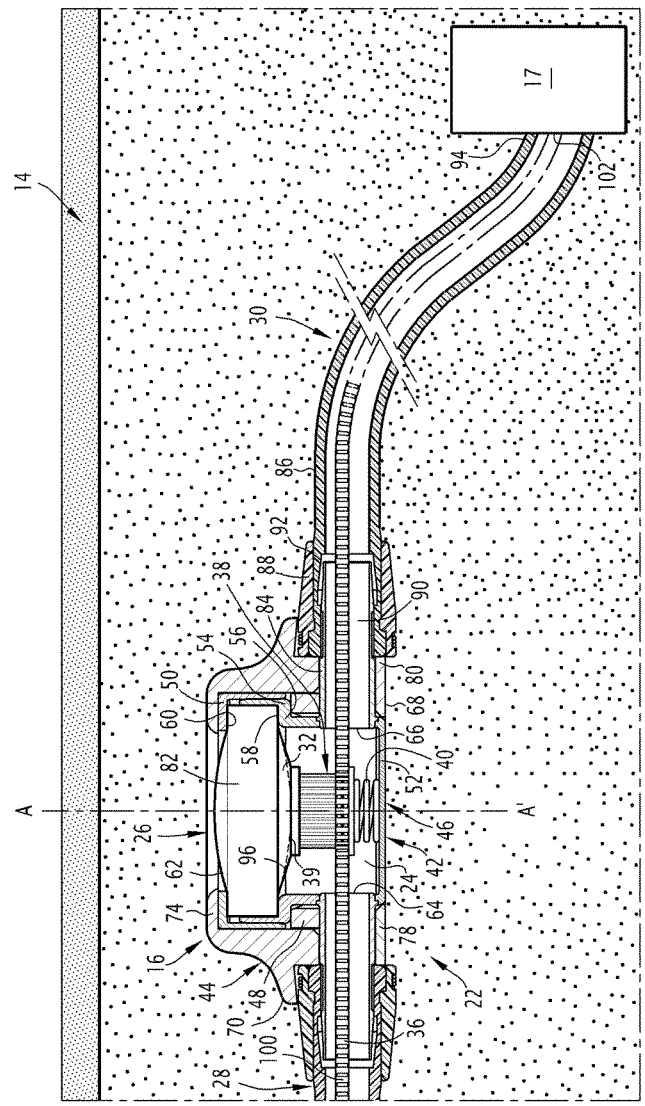
FIG. 3 is a view, in cross-section along a vertical median plane of the chamber of FIG. 1, including a drive mechanism and a toothed chain.
Figure 4:
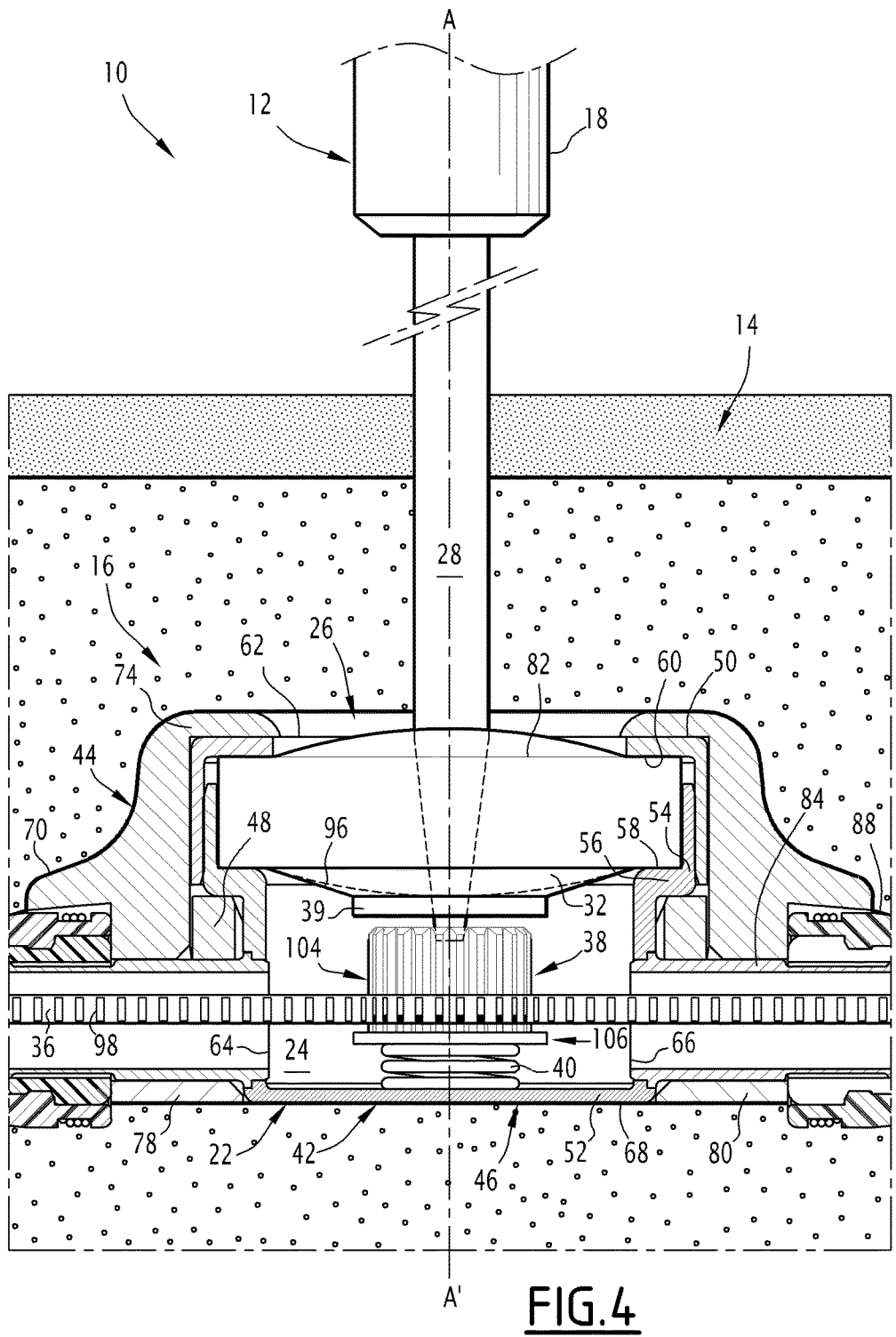
FIG. 4 is a view, in cross-section along a median vertical plane, of the kit of FIG. 1.

As illustrated by FIGS. 2 to 4, the chamber 16 includes a main body 22 delimiting an internal volume 24, a septum 26 closing the internal volume 24 and designed to be pierced by the region 20 of the tool 12. It defines at least one conduit 28, 30 projecting away from the main body 22. The conduit 28, 30 is rigid and secured to the main body 22.

In this example, the chamber 16 defines a first conduit 28 and a second conduit 30.

The chamber 16 further includes means for guiding the tool formed in this example by a centering cone 32 mounted below the septum 26 within the internal volume 24 of the main body 22.

The chamber 16 further includes a movable displacement member designed to actuate the external object, in this example formed by a toothed chain 36 capable of projecting outside the main body 22 through the conduits 28, 30 and a drive mechanism 38 for driving the displacement member, the mechanism being received in the internal volume 24 of the main body 22.

The chamber 16 further includes releasable means for locking the drive mechanism 38. These locking means here include a notched ring 39 for retaining the drive mechanism 38 mounted below the centering cone 32 within the internal volume 24 of the main body 22, and a biasing spring 40 situated below the drive mechanism 38 within the internal volume 24 of the main body 22.

The main body 22 includes an inner container 42 with a central axis A-A' and an outer peripheral shell 44 which, in this example, is snapped on the inner container 42.

In this example, the container 42 comprises a metal vat 46, a lower insert 48 mounted around the vat 46, and a retaining ring 50 for retaining the septum 26 positioned above the vat 46. Alternatively, the vat 46, the insert 48 and the ring 50 are made in a single piece.

The vat 46 is for example made from titanium. It includes a bottom 52 that delimits the bottom of the internal volume 24 and partially delimits that of the chamber 16, and a substantially cylindrical side wall 54 that laterally delimits the internal volume 24.

The side wall 54 has an annular shoulder 56 for bearing of the septum 26 that extends along its upper edge. This shoulder defines a lower surface 58 for gripping the septum 26.

The insert 48 extends around the side wall 54 of the vat, under the annular shoulder 56.

The ring 50 extends across from the annular shoulder 56 and defines an upper surface 60 for gripping the septum 26.

The internal volume 24 is delimited between the side wall 54 and the bottom of the vat 52. The volume 24 opens upward through a main upper opening 62 receiving the septum 26. It opens sideways through the side wall 54 of the vat by a first radial opening 64 and a second radial opening 66 for passage of the movable displacement member.

The insert 48 delimits two radial passages through which the movable displacement member extends.

The peripheral shell 44 is made from a plastic material, for example polyoxymethylene or POM. It extends around the insert 48 and the ring 50, to keep the ring 50 and the insert 48 in position on the vat 46.

The shell 44 has a lower surface 68 that is flush with the bottom 52 of the container 42 and a concave upper surface 70 that converges from top to bottom from the ring 50 toward a peripheral edge 72 of the shell 44 situated at the lower surface 68.

The shell 44 has a peripheral lip 74 that is substantially parallel to the lower surface 68, which bears on the ring 50 around the main opening 62.

The peripheral edge 72 delimits the outer contour of the chamber 16. In this example, this contour is substantially triangular.

The peripheral shell 44 further delimits through openings 76 for the passage of the suture thread, a first radial opening 78 and a second radial opening 80 for passage of the movable displacement member.

The radial opening 78 opens outward in register with the opening 64, which it extends radially relative to the axis A-A'. The radial opening 80 opens across from the opening 66, which it extends radially relative to the axis A-A'.

The septum 26 includes a main block 82, made from a tight material. The septum 26 is for example of the type described in application FR 10 52532 by the Applicant.

The block 82 has an outer contour with a shape substantially complementary to the contour of the upper opening 62.

The block 82 is gripped at its periphery between the ring 50 and the shoulder 56.

It upwardly sealably closes the internal volume 24. Thus, it prevents the bodily fluids and tissues from penetrating the internal volume 24. This protects the drive mechanism 38 and allows it to be kept in the body for significant length of time.

The block 82 is further capable of being pierced by the tool 12 when the drive mechanism 38 and the movable displacement member must be moved.

The first conduit 28 receives the movable displacement member.

It projects radially relative to the main body 22 through the radial opening 78 and beyond that radial opening 78. It is advantageously made with a base of a rigid conduit.

The second conduit 30 also receives the movable displacement member. It comprises a hollow rigid connector 84, a rigid tubing 86 and a crimping ring 88 for crimping the rigid tubing 86 on the rigid connector 84.

It projects radially relative to the main body 22 through the radial opening 80 and beyond that radial opening 80.

The tubing 86 is made with a base of a rigid plastic material. It has a length greater than the maximum transverse expanse of the main body 22, for example at least two times greater than that maximum expanse.

The tubing 86 extends between a first end 92 forcibly engaged around the free end of the rigid connector 84 and a second end 94 designed to be connected to the medical pump 17, situated in the body of the patient 11. The second end 94 defines a bearing point on the medical pump 17.

The centering cone 32 has an inner surface 96 that converges from top to bottom from the septum 26 toward the drive mechanism 38.

The centering cone 32 is capable of guiding the movement of the tool 12 toward a centering axis when the tool 12 has passed through the septum 26 from top to bottom, so as to center the tool 12 on the drive mechanism 38. It opens downward across from the mechanism 38. In this example, the centering axis of the centering cone 32 is combined with the axis A-A'.

Alternatively, the centering cone 32 is replaced by a centering tube having an inner surface with a constant section.

The notched ring 39 in this example includes a peripheral inner toothing. It is capable of engaging around the drive mechanism 38 to prevent the movement thereof.

In the example illustrated in FIGS. 3 and 4, the notched ring 39 is advantageously integral with the centering cone 32, which it extends downward.

Figure 5:
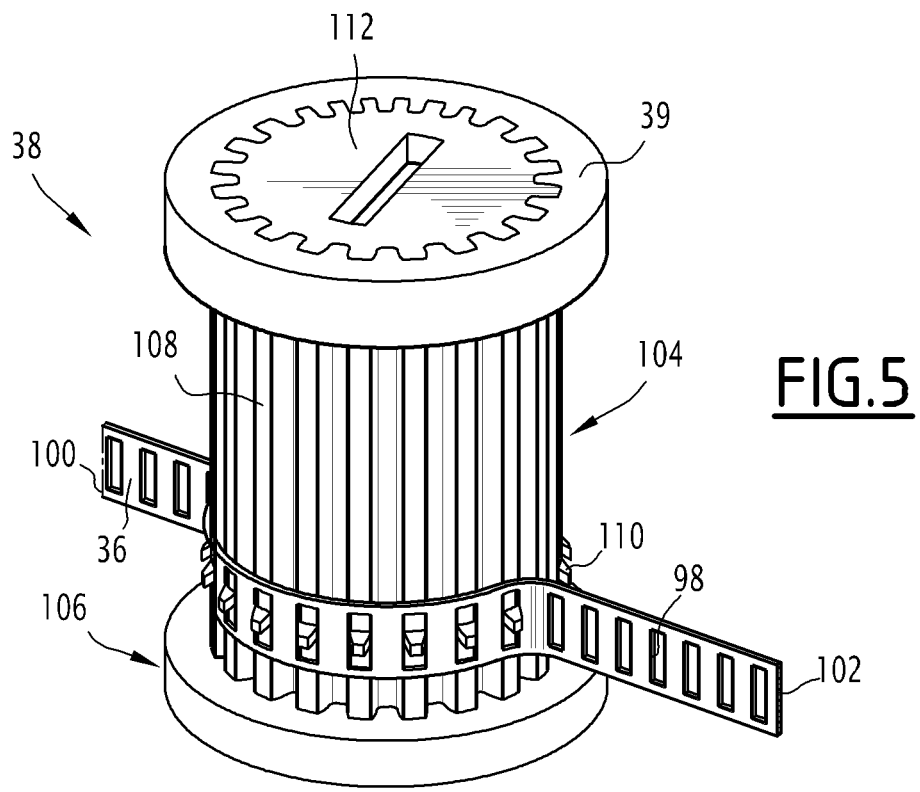
FIG. 5 is an outer perspective view of the drive mechanism of the chamber of FIG. 1, according to a first embodiment.

In reference to FIG. 5, the toothed chain 36 includes orifices 98 capable of cooperating with the drive mechanism 38. These orifices are formed by transverse slits spaced apart from one another along an axis of the chain.

The toothed chain 36 extends, through the first conduit 28, the internal volume 24 and the second conduit 30, respectively, between the first free end 100 and the second free end 102 connected to an actuator of the pump 17. The free end 102 is capable of going from a position separated from the chamber 16 to a position close to the chamber 16 to actuate the pump 17 while being driven by the drive mechanism 38.

Alternatively, the toothed chain 36 is replaced by a rack, the orifices 98 being replaced by notches capable of cooperating with the drive mechanism 38.

The drive mechanism 38 is capable of longitudinally moving along the axis A-A' between a locked position engaged on the ring 39 and a released position. In its released position, it is further capable of moving the toothed chain 36 relative to the main body 22.

As illustrated in FIGS. 4 and 5, the drive mechanism 38 includes a rotating member 104 and a stationary support 106 for guiding the rotating member.

The member 104 is rotatably mounted in the internal volume 24 of the chamber 16 around the axis A-A'.

The rotating member 104 includes a slotted cylinder 108 designed to cooperate with the ring 39, a toothed pinion 110 for driving the chain 36, and a head 112 provided with a housing for receiving the tool 12. The slotted cylinder 108, the toothed pinion 110 and the head 112 are advantageously integral.

The slotted cylinder 108 is capable of being inserted into the notched ring 39, the outer slots of the slotted cylinder 108 being parallel to the axis of rotation of the rotating member 104.

The toothed pinion 110 is capable of engaging in the orifices 98 of the toothed chain 36.

The head 112 is capable of cooperating with the distal region 20 of the tool 12.

The axis of rotation of the rotating member 104 is combined with the centering axis A-A' of the centering cone 32 such that the distal region 20 is guided toward the housing during insertion of the tool 12 through the septum 26.

In this example, the receiving housing assumes the form of a straight slot.

Figure 6:
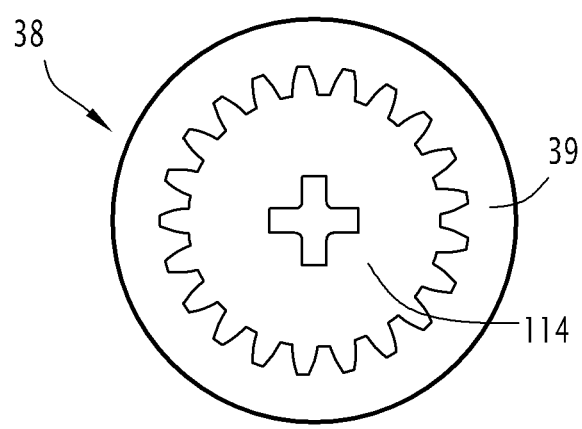
FIG. 6 is a top view of the drive mechanism of the chamber of FIG. 1, according to one alternative embodiment of the drive mechanism.

Alternatively and as shown in FIG. 6, the housing in the head 114 is cross-shaped.

The support 106 is for example formed by a pin protruding along the axis A-A' in the internal volume 24.

The spring 40 is inserted between the bottom of the vat 46 and the drive mechanism 38. It creates a permanent biasing force biasing the drive mechanism toward its locked position.

When the drive mechanism 38 is in its locked position, the spring 40 biases the drive mechanism 38, thereby keeping the rotating member 104 in the notched ring 39. The rotating member 104 is then locked in rotation around the axis A-A'.

When the drive mechanism 38 is in its released position, the spring 40 biases the drive mechanism toward its locked position. The rotating member 104 is released from the notched ring 39, and the rotation of the rotating member 104 is then possible.

The operation of the first kit 10 according to the invention will now be described.

Initially, as illustrated by FIG. 3, the implantable chamber 16 has been surgically positioned under the skin 14 of the patient 11. To that end, the chamber 16 is pressed against the tissues of the patient and is kept in position by suturing it through the through openings 76. The septum 26 is then placed across from the skin 14, in the vicinity thereof so as to receive the tool 12 easily.

The rigid tubing 86 is deployed in the body of the patient to connect the end 94 of the conduit 30 to the implantable pump 17. Inside the pump 17, the end 102 of the toothed chain 36 is engaged with an actuator of the pump 17.

Then, the skin 14 of the patient is put back in place, such that the chamber 16 is partially or completely concealed by the skin 14.

When the pump 17 must be actuated, for example to start it or modify its flow rate, the practitioner first performs an x-ray of the patient to view the exact position of the chamber 16 and its characteristics.

Next, the practitioner pierces the skin 14 of the patient with the distal region 20 of the tool 12. He then passes through the septum 26, while grasping the proximal maneuvering region 18 of the tool 12 to bring the distal region 20 of the tool 12 into the internal volume 24.

The practitioner moves the tool 12 along the centering axis A-A' of the centering cone 32, until the head of the tool 12 is inserted into the housing of the head 112 of the rotating member 104.

The practitioner next applies a force oriented toward the bottom of the vat 46 along the axis A-A' to compress the spring 40 and move the rotating member 104 toward the released position. The rotating member 104 is then freed from the notched ring 39.

The practitioner next imparts a rotational movement to the drive mechanism 38 via the tool 12. The toothed chain 36 then moves longitudinally in the conduit 30.

This movement commands the pump 17, to activate it, stop it, or modify its flow rate.

One can see that the pump 17 is started remotely by the practitioner, and with minimal risk of infection for the patient. In fact, only an incision using the tool 12 is necessary to actuate the pump 17.

Figure 7:
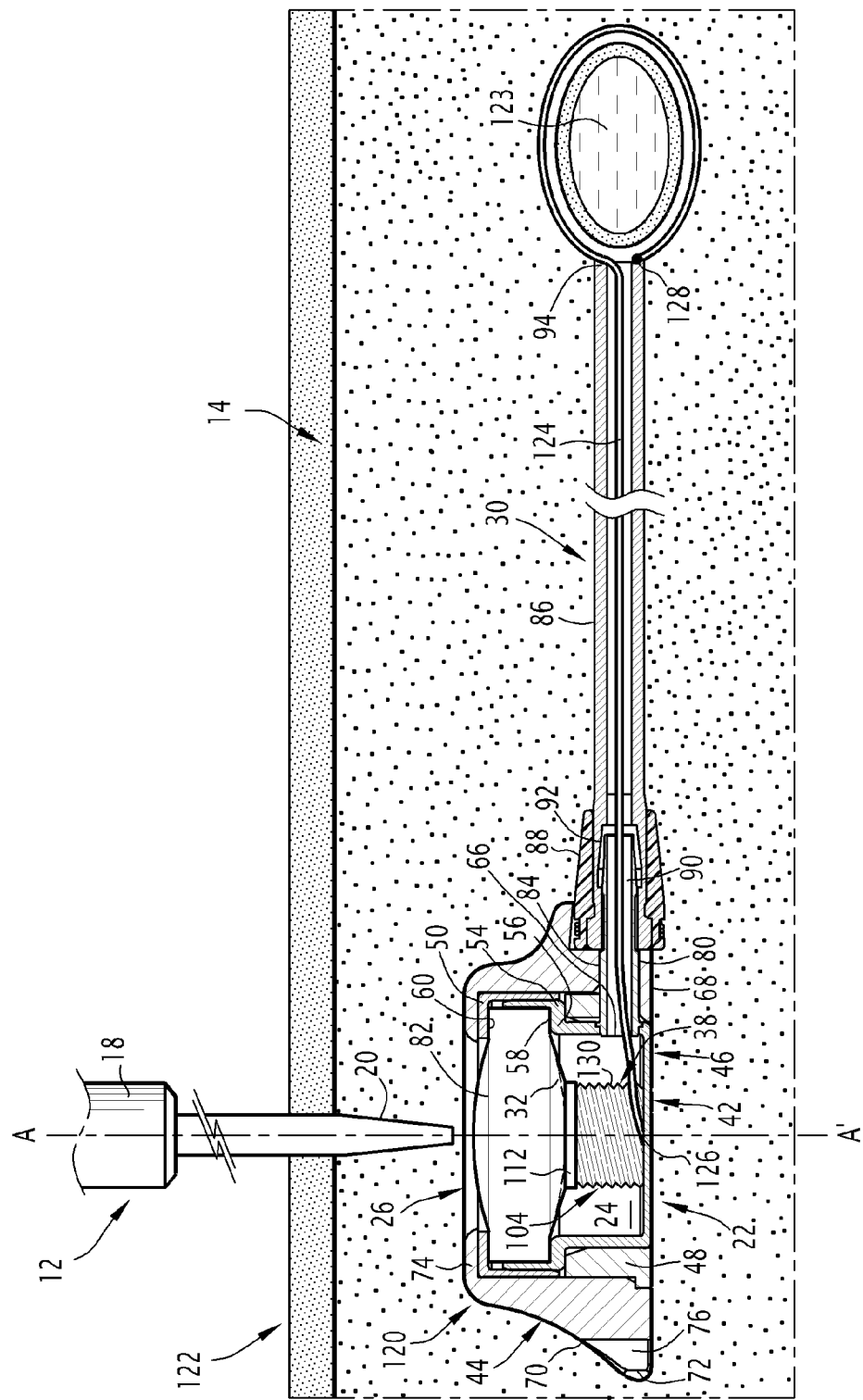
FIGS. 7, 8 and 9 are views similar to FIG. 3 of a second kit according to the invention.
Figure 8:
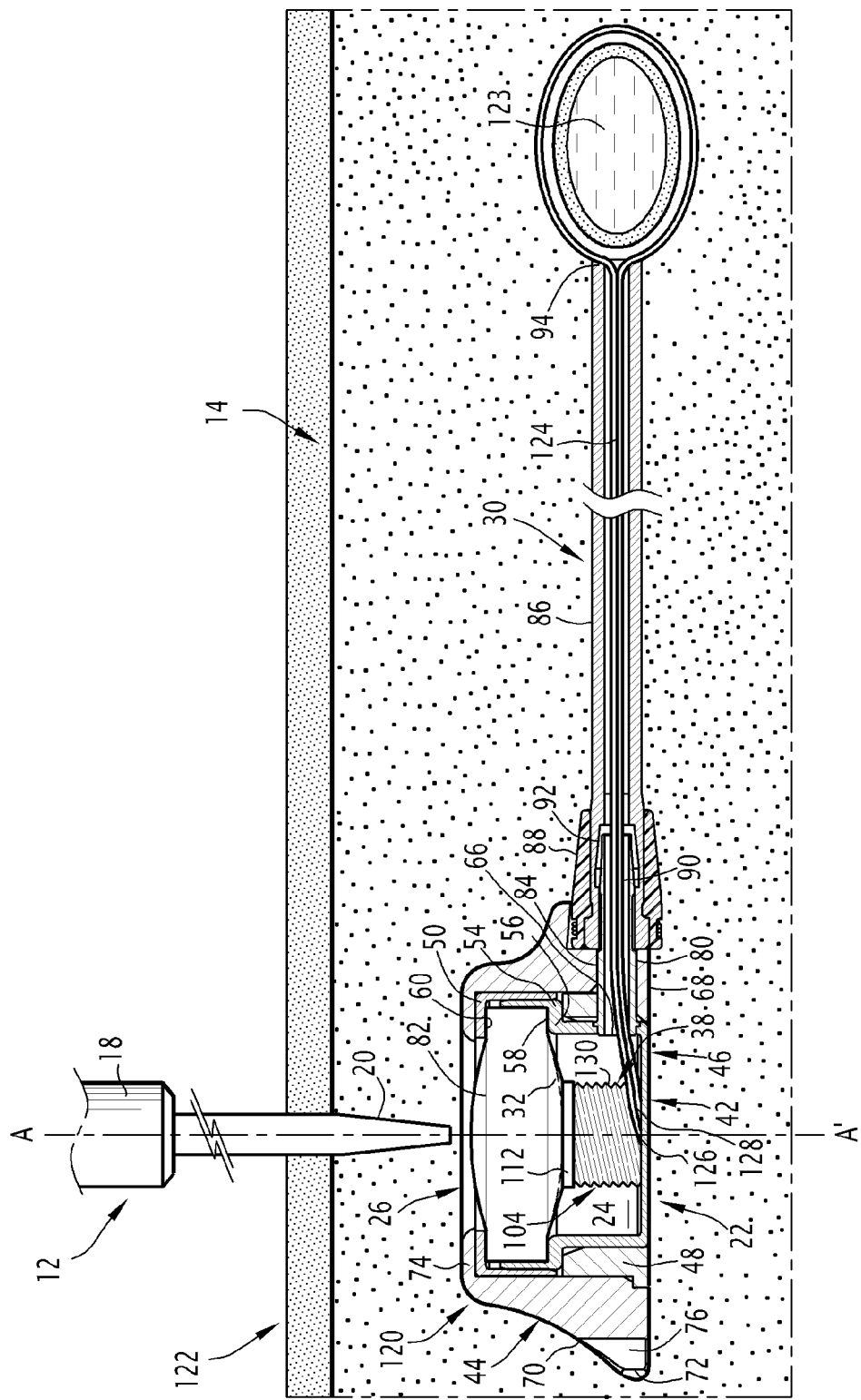
Figure 9:
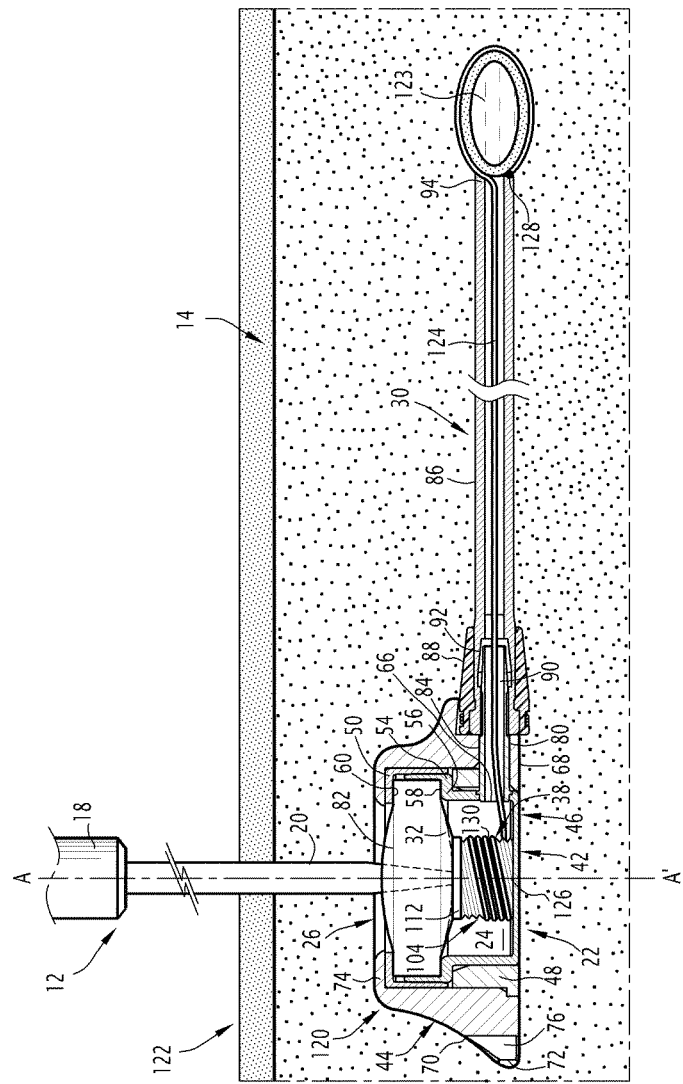

The chamber 120 of a second kit 122 according to the invention is shown in FIGS. 7, 8 and 9.

Such a chamber 120 is in particular capable of remotely ligating an organ 123 or blood vessel of the patient 11.

Unlike the chamber 16 of the first kit 10, the chamber 120 only includes a single passage conduit 30 projecting away from the main body 22. The conduit 30 is rigid and secured to the main body 22.

The tubing 86 extends between a first end 92 forcibly engaged around the free end of the rigid connector 84 and a second free end 94 designed to be placed in the immediate vicinity of the organ 123 to be ligated.

Furthermore, the movable displacement member is formed by a thread 124, capable of projecting outside the main body 22 through the conduit 30. The thread 124 extends, inside the internal volume 24 and the conduit 30, between a first end 126 fastened to the rotating body 104 and a second end 128 fastened on the free end 94 of the tubing 86.

At its distal end, the thread 124 defines a tightening loop with a variable active length surrounding the member 123.

Alternatively, and as illustrated in FIG. 8, the thread 124 extends between a first end 126 and a second end 128, the two ends 126, 128 being fastened to the rotating member 104. The thread 124 defines a tightening loop with a variable active length surrounding the member 123 in a region substantially close to the middle of the thread.

Unlike the chamber 16 of the first kit 10, the chamber 120 does not include any notched ring or spring.

Furthermore, the rotating member 104 includes a threaded cylinder 130 and a head 112 provided with a housing for receiving the tool 12. The threaded cylinder 130 and the head 112 are advantageously integral. Unlike the chamber 16 of the first kit 10, the rotating member 104 does not include any toothed pinion.

The outer threading of the cylinder 130 defines a helical slot for winding the movable displacement member, designed to receive the thread.

Initially and as illustrated in FIG. 7, the thread 124 grips the member 123, which is not compressed.

When the practitioner wishes to ligate the organ 123 locally, he first takes an x-ray of the patient to view the exact position of the chamber 120 and its characteristics.

As illustrated in FIG. 9, the practitioner inserts the tool 12 through the skin 14 of the patient and passes through the septum 26, while grasping the proximal maneuvering region 18 of the tool 12 to bring the distal region 20 of the tool 12 into the internal volume 24.

The practitioner then moves the tool 12 along the centering axis of the centering cone 32, until the head of the tool 12 is inserted into the housing of the head 112 of the rotating member 104.

The practitioner imparts a rotational movement to the drive mechanism 38 via the tool 12, to set the thread 124 in motion. This motion winds an increasing length of thread around the cylinder 130, causing a decrease in the length of the thread situated outside the chamber 120.

In reference to FIG. 9, the active length of the tightening loop then decreases, causing local gripping of the organ 123.

Conversely, by rotating the drive mechanism 38 in an opposite direction, the thread 124 unwinds outside the cylinder 130.

The active length of the tightening loop then increases, allowing deployment of the organ 123.

Owing to the invention described above, one can see that the implantable chamber according to the invention has improved functionalities, for example remote actuation of a pump implanted within a patient, or remote ligating of an organ or a blood vessel using a displacement member actuated by a mechanism received in the internal volume of the chamber. The implantable chamber according to the invention also avoids cell colonization inside the internal volume of the chamber, and thereby protects the drive mechanism. It lastly limits the risks of infection for the patient.

As clearly shown in the figures, the movement member 36, 124 is capable of actuating or setting in motion an element 17, 123 situated in the body of the patient 11, without having to simultaneously inject fluid through the movement member 36, 124.

Furthermore, the active length of the displacement member 36, 124 capable of being extracted outside the main body 22 in the conduit 28, 30 is greater than the maximum transverse expanse of the main body 22, in particular greater than two times the transverse expanse of the main body 22. This makes it possible to actuate the elements that are remote from the chamber 16, 120, beyond the immediate vicinity of the chamber 16, 120.

What is more, the displacement member 36, 124 can be extracted outside the conduit 28, 30 over a significant length, for example greater than 0.5 times the length of the conduit 28, 30.

The invention claimed is:

1. A kit for remotely maneuvering an element present in the body of a patient, of the type comprising:
    an implantable chamber designed to be placed under the skin of a patient, comprising:
    a hollow main body delimiting an internal volume, the internal volume opening outwards via a main opening,
    a septum, wherein the septum is mounted on the main body to close the main opening,
    at least one conduit projecting away from the main body,
    a belt, wherein the belt is configured to be movable relative to the main body, wherein the belt is configured to project from the main body via the or each conduit and capable of actuating or setting in motion an element situated in the body of the patient, said belt extending the entire length of the at least one conduit,
    a drive, wherein the drive is configured to drive the belt situated in the internal volume of the main body, in order to move the belt with respect to the main body, the main body comprising an inner container with a central axis and an outer peripheral shell snapped on the inner container, said inner container comprising a metal vat, a lower insert mounted around the vat, and a retaining ring for the septum positioned above the vat, the internal volume being determined by the vat, and
    a tool comprising a proximal maneuvering region and a distal region configured to pierce the septum to actuate the drive.

2. A method for remotely maneuvering an element present in the body of a patient, comprising the following steps:
    providing a kit according to claim 1,
    piercing the tool through the septum to insert the distal region of the tool into the internal volume,
    engaging the tool on the drive,
    actuating the drive using the tool to move the belt.

3. An implantable chamber designed to be placed under the skin of a patient, comprising:
    a hollow main body delimiting an internal volume, the internal volume opening outwards via a main opening,
    a septum, wherein the septum is mounted on the main body to close the main opening,
    at least one conduit projecting away from the main body,
    a belt, wherein the belt is configured to be movable relative to the main body, wherein the belt is configured to project from the main body via the at least one conduit and configured to actuate or set in motion an element situated in the body of the patient, and
    a drive, wherein the drive is configured to drive the belt situated in the internal volume of the main body, in order to move the belt respect to the main body,
    the main body comprising an inner container with a central axis and an outer peripheral shell snapped on the inner container, said inner container comprising a metal vat, a lower insert mounted around the vat, and a retaining ring for retaining the septum positioned above the vat, the internal volume being delimited by the vat.

4. The implantable chamber of claim 3, wherein the drive comprises a threaded cylinder and the belt is wound in a helical slot of the threaded cylinder without a toothed pinion.

5. The implantable chamber of claim 3, further comprising a solid piece having an open center axis, wherein the solid piece having an open center axis is mounted below the septum within the internal volume of the main body, the solid piece having an open center axis being configured to guide the movement of a tool longitudinally along a centering axis, wherein the septum is configured to be pierced by the tool and the drive is configured to cooperate with the tool.

6. The implantable chamber of claim 5, wherein the solid piece having an open center axis comprises an inner surface converging toward a centering opening situated in register with the drive.

7. The implantable chamber of claim 3, wherein the drive comprises a toothed wheel, wherein the toothed wheel is mounted in the internal volume, the belt being engaged on the toothed wheel.

8. The implantable chamber of claim 7, wherein the toothed wheel comprises a head delimiting a housing for receiving a tool for actuating the drive.

9. The implantable chamber of claim 7, wherein the toothed wheel has a pinion, the belt defining orifices spaced along its length to cooperate with the pinion on the toothed wheel.

10. The implantable chamber of claim 7, wherein the belt comprises notches configured to cooperate with the toothed wheel.

11. The implantable chamber of claim 7, wherein the belt comprises spaced openings engaged on the toothed wheel.

12. The implantable chamber of claim 3, further comprising a lock, wherein the lock is configured to lock the drive situated within the internal volume of the main body, the lock being configured to be released when the actuating tool for actuating the drive is inserted.

13. The implantable chamber of claim 12, wherein the drive further comprises a drive configured to drive the belt, movable between a locked position and a released position, wherein the lock is configured to engage the belt in the locked position, and
an elastic bias, wherein the elastic bias is configured to bias the belt toward its locked position.

14. The implantable chamber of claim 3, wherein the belt is comprised of a flexible component.

15. The implantable chamber of claim 14, wherein the flexible component is a chain, a rack or a thread.

16. The implantable chamber of claim 3, wherein the at least one conduit comprises a rigid tubing having a length at least two times greater than the maximum expanse of the main body.

* * * * *